United States Patent
Abraham-Fuchs et al.

(10) Patent No.: US 6,484,104 B2
(45) Date of Patent: Nov. 19, 2002

(54) NETWORK FOR EVALUATING DATA OBTAINED IN A BIOCHIP MEASUREMENT DEVICE

(76) Inventors: Klaus Abraham-Fuchs, Graslitzerstr. 17, 91058 Erlangen (DE); Arne Hengerer, Wesh. Stadtmaurer-Str. 40, 91054 Erlangen (DE); Norbert Windhab, Hamedstraus 36, D-65419 Hofhein (DE); Kieran Gallahue, 4746 Shadwell Pl., San Diego, CA (US) 92130; James P. O'Conell, 166 Solana Point Cir., Solana Beach, CA (US) 92075; Greg Gosch, 2910 Corte Celeste, Carlsbad, CA (US) 92009

( * ) Notice: Subject to any disclaimer, the term of this patent is extended or adjusted under 35 U.S.C. 154(b) by 37 days.

(21) Appl. No.: 09/784,571

(22) Filed: Feb. 15, 2001

(65) Prior Publication Data

US 2002/0111741 A1 Aug. 15, 2002

(51) Int. Cl.⁷ .................................................. G06F 3/00
(52) U.S. Cl. ......................................... 702/19; 702/188
(58) Field of Search ..................... 702/19, 188; 435/92, 435/99, 91

(56) References Cited

U.S. PATENT DOCUMENTS

| | | | | |
|---|---|---|---|---|
| 5,594,663 A | * | 1/1997 | Messaros et al. | 364/550 |
| 6,142,681 A | * | 11/2000 | Gulati | 395/13 |
| 6,175,752 B1 | * | 1/2001 | Say et al. | 600/345 |
| 6,366,871 B1 | * | 4/2002 | Geva | 702/188 |

* cited by examiner

*Primary Examiner*—Marc S. Hoff
*Assistant Examiner*—Felix Suarez
(74) *Attorney, Agent, or Firm*—Schiff Hardin & Waite

(57) ABSTRACT

In a network and a method for evaluating medical data, a disposable biochip is provided which contains a patient sample with multiple biomolecular markers, as well as a biochip identifier which characterizes the biochip. The biochip is inserted into a point of care test device, which reads the biochip identifier. The point of care test device transmits the data characterizing the biochip to a remote server having access to a data bank in which a large number of measurement protocols are stored, and which selects one of the measurement protocols for testing the sample based on the transmitted data characterizing the biochip. The measurement protocol is transmitted back to the point of care test device via the data link, where the sample is tested using the measurement protocol. The test results are evaluated in an expert system, and a diagnostic result is displayed at the point of care test device.

6 Claims, 1 Drawing Sheet

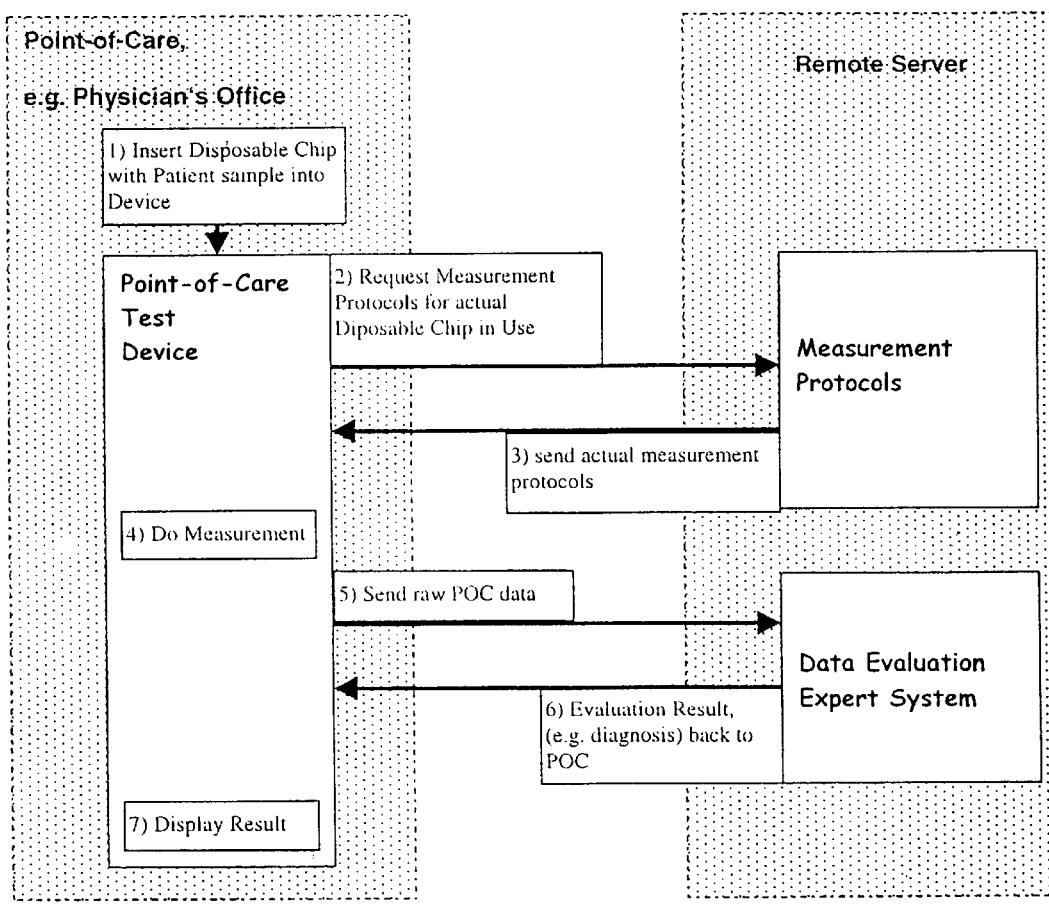

NETWORK FOR EVALUATING DATA OBTAINED IN A BIOCHIP MEASUREMENT DEVICE

BACKGROUND OF THE INVENTION

1. Field of the Invention

The present invention is directed to an arrangement for reading and evaluating data from a biosensor array (biochip) for medical diagnostic purposes.

2. Description of the Prior Art

It is well-known that the presence of certain biomolecules, such as a particular protein, antibody or DNA fragment, in the human body is correlated with certain diseases, and therefor it is also known to make a medical diagnosis based on identification of the presence of these biomolecules. If the presence of a certain molecular species at a certain concentration level in the human body has been shown to be correlated with the presence or absence of a particular pathology (disease), the relevant biomolecule is referred to as a diagnostic marker for the pathology. For most diseases, the pathological reaction chain is very complex, and involves a large number of different biomolecules which, in turn, also may play a role in the pathophysiology of another disease. Therefore, a single marker is not always sufficient in order to unequivocally diagnose a particular disease. Often, it is only through an evaluation protocol involving several combined markers that a diagnosis can be made. For example, if a concentration is high for a first marker, low for a second marker, and a third marker is absent, then a particular disease can be diagnosed. The measurement of single markers or multiple markers is referred to as an in vitro diagnostic test. The development of markers for such diagnostic tests is very cost intensive and time intensive, and the development of expert rules for such tests is even more cost intensive and time intensive.

A new generation of biosensor arrays has been developed and is about to enter widespread use in the medical diagnostic market. Instead of conducting multiple measurements of multiple markers with a number of different devices, or using highly sophisticated robots in a centralized diagnostic laboratory, the new generation of biosensor arrays are able to measure, in a fully automated manner, a large number of markers simultaneously, up to thousands of different markers on the same chip, without a need for further human interaction. Moreover, such measurement are made outside of a formal laboratory environment. Almost all known types of biomolecular markers (e.g. DNA fragments, proteins, enzymes, antibodies, etc.) can be measured simultaneously on the same chip. These biochips are particularly suited for immediately conducting the diagnostic test at a point of care (POC) site, such as a hospital bedside, a physician's office, or even at the patient's home. Such biochips also, of course, can be used in a professional centralized laboratory.

In such multi-marker biochips, the measurement procedure also becomes increasingly complex. Before starting the actual measurement, it is often necessary to conduct a sample preparation cycle, involving a chemical reaction, filtering, etc. During the measurement itself, certain boundary conditions, such as a stable temperature or a temperature time gradient or a certain bias potential at an electrode might be necessary in order to optimize or standardize the measurement result. The complete time sequence of all settings (chemical, electrical, mechanical) is referred to as a measurement protocol. A measurement protocol, moreover, can change, and likely will change, with every configuration of markers on a biochip, and may even be optimized during the life cycle of a given biochip configuration, as new and improved knowledge becomes available in the field. This requires fast and flexible ways to update measurement protocols at measurement devices in the field, i.e., testing and measurement devices located at point of care sites.

Since the number of pathologies or diseases which may have to be tested for at a point of care site is relatively large, it is very difficult for a point of care administrator to keep track of all of the different measurement protocols which are respectively necessary for these different diseases and pathologies, as well as to be sure that each protocol is up-to-date and/or matched to the version of the biochip which is being employed. For example, even though a particular measurement protocol may have been updated, the particular biochip being employed for a test, if it has been an inventory for a certain amount of time, may not be compatible with the most current protocol, but may require an "out-of-date" (but still approved) measurement protocol.

Because of the complexity and number of such in vitro tests, conventionally the majority of in vitro tests are conducted at centralized laboratories, with evaluations being made by experience laboratory personnel.

SUMMARY OF THE INVENTION

It is an object of the present invention to provide a network for evaluating medical data which allows a point of care test device to receive a biochip with a patient's sample and to obtain the relevant diagnostic data, without the necessity of resorting to the use of a centralized laboratory.

The above object is achieved in accordance with the principles of the present invention in a network and a method wherein a biochip having a patient's sample is identified with a biochip identifier, such as a bar code, which includes the relevant information as to the type of pathology or disease which is to be tested using the biochip's sample and/or an identification of the version of the biochip (in terms of successively developed modifications). The biochip is inserted in a point of care test device, which is in communication via a data link with a remote server. At the remote server, a number of measurement protocols are stored, either in a memory at the server or a memory accessible by the server. The various measurement protocols are not only different protocols for different diseases and pathologies, but are also different updates of the same protocol for the same disease or pathology. Based on the biochip identifier which is transmitted by the point of care test device to the remote server, the appropriate measurement protocol is selected and is transmitted back to the point of care test device via the data link.

The point of care test device then conducts the test on the sample in the biochip using the transmitted protocol, to obtain test result data.

Two options are available for evaluating the test result data. The point of care test device itself may contain sufficient software in order to evaluate the test result data at the point of care site. Alternatively, the test result data can be transmitted via the data link to the remote server, and the remote server can be provided with an evaluation unit, such as an expert evaluation system, which evaluates the test result data and transmits the diagnostic result back to the point of care test device via the data link.

DESCRIPTION OF THE DRAWING

The single FIGURE is a flowchart showing the basic steps and components in the method and network of the invention.

DESCRIPTION OF THE PREFERRED EMBODIMENTS

As shown in the FIGURE, a test device is provided at a point of care location, such as a physician's office. The test device is for performing a test according to a measurement protocol on a patient sample which is contained in a disposable biochip which is inserted into the test device (step 1). The disposable biochip has a bar code thereon which is read at the test device and which identifies the type of disease or pathology which is to be tested for, and also identifies the version of the biochip containing the sample to be tested. The biochip identifier, represented by the bar code, is transmitted from the point of care test device via a data link to a remote server in the form of a request for a measurement protocol for the particular disposable biochip which is currently inserted in the test device (step 2).

The remote server contains, or has access to, a data bank containing a large number of measurement protocols for many different diseases and pathologies, as well as different updated version of the same protocol for a particular disease or pathology. Based on the biochip identifier transmitted from the point of care test device, the remote server selects the appropriate measurement protocol for use with the currently-inserted biochip, and transmits this measurement protocol via the data link back to the point of care test device (step 3).

The point of care test device then conducts the measurement according to the transmitted protocol (step 4) and thereby obtains raw point of care data.

Depending on the complexity of the analysis which is required for the raw point of care data, the evaluation thereof can take place at the point of care location, even in the point of care test device, if the test device, or some other evaluation unit at the point of care site contains appropriate software.

Another alternative is to transmit the raw point of care data via the data link to the remote server. At the remote server, an expert data evaluation system is present which analyzes the raw point of care data and obtains an evaluation result (diagnosis) which is then transmitted back to the point of care location via the data link (step 6).

The result of the evaluation, obtained either at the point of care site or from the remote server, is then displayed at the point of care location (step 7).

The point of care test device is thereby relieved of the necessity of being continually updated and modified to add different measurement protocols and to update existing measurement protocols. Moreover, even if an inventory of biochips is maintained at the point of care site, so that a biochip might be inserted in the test device which is currently "out-of-date" (but still approved for use), the measurement protocol data bank at the remote server can recognize this fact and still provide an approved measurement protocol, which may not necessarily be the most current protocol update.

Of course, the data link between the point of care site and the remote server can be protected, as warranted, with appropriate encryption or other security techniques. Also, the usual patient consent and agreements between the patient and physician will be obtained in order to allow transfer of patient information from the point of care site to the remote server, and appropriate access control (or denial) at the remote server must be implemented as well.

Although modifications and changes may be suggested by those skilled in the art, it is the intention of the inventors to embody within the patent warranted hereon all changes and modifications as reasonably and properly come within the scope of their contribution to the art.

We claim as our invention:

1. A network for evaluating medical data, comprising:
    a disposable biochip containing a patient sample with multiple biomolecular markers, said biochip also containing a biochip identifier characterizing at least a version of said biochip;
    a point of care test device into which said biochip is insertable, said point of care test device including a reader for said identifier to obtain data characterizing said biochip;
    a remote server;
    a data link allowing communication between said point of care test device and said remote server, said point of care test device transmitting said data characterizing said biochip via said data link to said remote server upon insertion of said biochip into said point of care test device;
    a data bank accessible from said remote server containing a plurality of measurement protocols, said remote server, based on said data characterizing said biochip, selecting one of said measurement protocols for use in testing said sample in said biochip and transmitting said measurement protocol back to said point of care test device via said data link;
    said point of care test device receiving said measurement protocol and testing said sample using said measurement protocol to obtain test data;
    an expert system supplied with said test data for evaluating said test data to produce a diagnostic result; and
    a display at said point of care test device for displaying said diagnostic result.

2. A network as claimed in claim 1 wherein said expert system is located at said remote server, and wherein said point of care test device transmits said test results to said expert system at said remote server via said data link, and wherein said remote server transmits said evaluation result back to said point of care test device via said data link.

3. A network as claimed in claim 1 wherein said expert system is located at said point of care test device.

4. A method for evaluating medical data, comprising the steps of:
    obtaining a patient sample with multiple biomolecular markers and storing said sample in a disposable biochip containing a biochip identifier characterizing at least a version of said biochip;
    inserting said biochip into a point of care test device and, in said point of care test device, reading said biochip identifier to obtain data characterizing said biochip;
    establishing a data link between said point of care test device and a remote server and transmitting said data characterizing said biochip via said data link to said remote server upon insertion of said biochip into said point of care test device;
    storing a plurality of measurement protocols in a data bank accessible from said remote server;
    via said remote server, selecting one of said measurement protocols from said data bank for use in testing said sample in said biochip dependent on said data characterizing said biochip, and transmitting said measurement protocol back to said point of care test device via said data link;
    testing said sample in said biochip at said point of care test device using said measurement protocol to obtain test data;

evaluating said test data in an expert system to obtain a diagnostic result; and displaying said diagnostic result at said point of care test device.

5. A method as claimed in claim 4 comprising disposing said expert system at said remote server, and transmitting said test result from said point of care test device to said expert system via said data link and transmitting said diagnostic result from said expert system back to said point of care test device via said data link.

6. A method as claimed in claim 4 comprising disposing said expert system at said point of care test device.

\* \* \* \* \*